United States Patent [19]

McCormack

[11] Patent Number: 5,843,057
[45] Date of Patent: Dec. 1, 1998

[54] FILM-NONWOVEN LAMINATE CONTAINING AN ADHESIVELY-REINFORCED STRETCH-THINNED FILM

[75] Inventor: Ann Louise McCormack, Cumming, Ga.

[73] Assignee: Kimberly-Clark Worldwide, Inc., Neenah, Wis.

[21] Appl. No.: 882,715

[22] Filed: Jun. 25, 1997

Related U.S. Application Data

[60] Provisional application No. 60/021,733 Jul. 15, 1996.

[51] Int. Cl.$^6$ .............................. A61F 13/15; B32B 7/00
[52] U.S. Cl. .......................... 604/367; 442/76; 442/400; 442/401; 442/393; 442/382; 128/849; 2/904
[58] Field of Search .............................. 604/367; 442/76, 442/400, 401, 393, 382; 128/849; 2/904

[56] References Cited

U.S. PATENT DOCUMENTS

| | | | |
|---|---|---|---|
| 2,949,394 | 8/1960 | Rodman | 154/50 |
| 3,338,992 | 8/1967 | Kinney | 264/24 |
| 3,341,394 | 9/1967 | Kinney | 161/72 |

(List continued on next page.)

FOREIGN PATENT DOCUMENTS

| | | | |
|---|---|---|---|
| 0 123 426 | 10/1984 | European Pat. Off. . | |
| 0 179 162 | 10/1984 | European Pat. Off. . | |
| 0 301 624 | 2/1989 | European Pat. Off. . | |
| 0 320 314 | 6/1989 | European Pat. Off. . | |
| 0 372 363 | 6/1990 | European Pat. Off. . | |
| 0 391 661 | 10/1990 | European Pat. Off. . | |
| 0 403 187 | 12/1990 | European Pat. Off. | B32B 5/18 |
| 0 472 436 | 2/1992 | European Pat. Off. | B32B 5/28 |
| 0 505 027 | 9/1992 | European Pat. Off. . | |
| 0 556 749 | 8/1993 | European Pat. Off. | A61F 13/15 |
| 0 599 425 | 6/1994 | European Pat. Off. | A24F 23/02 |
| 0 604 731 | 7/1994 | European Pat. Off. . | |
| 0 642 922 | 3/1995 | European Pat. Off. | B32B 31/08 |
| 0 691 203 | 1/1996 | European Pat. Off. . | |
| 0 716 917 | 6/1996 | European Pat. Off. | B32B 27/32 |
| 2 145 611 | 2/1973 | France | B32B 5/00 |
| 2 728 280 | 12/1995 | France . | |
| 2 141 988 | 3/1972 | Germany | A41B 13/02 |
| 26 07 331 | 9/1977 | Germany | B32B 27/12 |
| 6 912 926 | 3/1971 | Netherlands | B32B 27/12 |
| 1 204 825 | 9/1970 | United Kingdom | B32B 27/12 |
| 1 360 115 | 7/1974 | United Kingdom | B29D 7/00 |
| 1 360 496 | 7/1974 | United Kingdom | B32B 27/12 |
| 1 377 801 | 12/1974 | United Kingdom | A41B 13/02 |
| 1 595 393 | 8/1981 | United Kingdom | B32B 5/18 |
| 2 285 066 | 12/1994 | United Kingdom . | |
| 89/10840 | 11/1989 | WIPO | B32B 27/12 |
| 90/14949 | 12/1990 | WIPO | B32B 31/08 |
| 93/06183 | 4/1993 | WIPO | C09J 7/02 |
| 93/21013 | 10/1993 | WIPO | B32B 27/12 |
| 94/23947 | 10/1994 | WIPO | B32B 27/12 |
| 95/16562 | 6/1995 | WIPO | B32B 5/24 |
| 96/09165 | 3/1996 | WIPO | B32B 27/12 |
| 96/19346 | 6/1996 | WIPO . | |

OTHER PUBLICATIONS

"An Improved Device for the Formation of Superfine, Thermoplastic Fibers", K. D. Lawrence, R. T. Lucas, J. A. Young, NRL Report 5265, Feb. 1959.

"Manufacture of Superfine Organic Fibers", V. A. Wente, E. L. Boone, C. D. Fluharty, NRL Report 4364, May 1954.

Primary Examiner—Robert A. Clarke
Attorney, Agent, or Firm—Nicholas N. Leach; James B. Robinson

[57] ABSTRACT

The present invention is directed to film-nonwoven laminates incorporating stretch-thinned, breathable films onto which a pattern or network of adhesive areas is applied to improve durability and strength of the stretch-thinned film. The present invention has applicability in a wide variety of areas where strength, comfort, liquid impermeability and breathability are needed or desired, including without limitation, personal care absorbent articles, articles of clothing, roll goods and health care-related items.

22 Claims, 3 Drawing Sheets

U.S. PATENT DOCUMENTS

| | | | |
|---|---|---|---|
| 3,342,613 | 9/1967 | Schelhorn | 99/171 |
| 3,423,266 | 1/1969 | Davies et al. | 156/167 |
| 3,502,538 | 3/1970 | Petersen | 161/150 |
| 3,542,615 | 11/1970 | Dobo et al. | 156/181 |
| 3,622,434 | 11/1971 | Newman | 161/128 |
| 3,654,060 | 4/1972 | Goldman | 161/112 |
| 3,676,242 | 7/1972 | Prentice | 156/62.4 |
| 3,692,618 | 9/1972 | Dorschner et al. | 161/72 |
| 3,779,246 | 12/1973 | Mesek et al. | 128/287 |
| 3,802,817 | 4/1974 | Matsuki et al. | 425/66 |
| 3,849,241 | 11/1974 | Butin et al. | 161/169 |
| 4,041,203 | 8/1977 | Brock et al. | 428/157 |
| 4,069,822 | 1/1978 | Buell | 128/294 |
| 4,147,580 | 4/1979 | Buell | 156/291 |
| 4,178,407 | 12/1979 | Rubens | 428/284 |
| 4,210,144 | 7/1980 | Sarge, III et al. | 128/287 |
| 4,340,563 | 7/1982 | Appel et al. | 264/518 |
| 4,444,822 | 4/1984 | Doyle et al. | 428/109 |
| 4,483,895 | 11/1984 | Deaver | 428/198 |
| 4,526,577 | 7/1985 | Schmidt, Jr. et al. | 604/366 |
| 4,587,175 | 5/1986 | Akao | 428/596 |
| 4,606,970 | 8/1986 | Sharps, Jr. | 428/301 |
| 4,658,958 | 4/1987 | McNulty et al. | 206/328 |
| 4,677,695 | 7/1987 | Van Gompel et al. | 2/79 |
| 4,687,692 | 8/1987 | Akao | 428/137 |
| 4,704,116 | 11/1987 | Enloe | 604/385 A |
| 4,720,252 | 1/1988 | Appel et al. | 425/80.1 |
| 4,725,473 | 2/1988 | Van Gomel et al. | 428/156 |
| 4,748,070 | 5/1988 | Beehler | 428/198 |
| 4,769,024 | 9/1988 | Pike et al. | 604/390 |
| 4,828,556 | 5/1989 | Braun et al. | 604/365 |
| 4,833,010 | 5/1989 | Langley | 428/287 |
| 4,849,049 | 7/1989 | Colton | 156/291 |
| 4,855,178 | 8/1989 | Langley | 428/287 |
| 4,865,908 | 9/1989 | Liu et al. | 428/248 |
| 4,886,697 | 12/1989 | Perdelwitz, Jr. et al. | 428/192 |
| 4,891,249 | 1/1990 | McIntyre | 427/421 |
| 4,892,769 | 1/1990 | Perdelwitz, Jr. et al. | 428/68 |
| 4,900,377 | 2/1990 | Redford et al. | 156/62.2 |
| 4,900,390 | 2/1990 | Colton et al. | 156/291 |
| 4,935,287 | 6/1990 | Johnson et al. | 428/198 |
| 4,945,848 | 8/1990 | Linville | 114/103 |
| 4,952,441 | 8/1990 | Bose et al. | 428/121 |
| 5,036,551 | 8/1991 | Dailey et al. | 2/167 |
| 5,064,492 | 11/1991 | Friesch | 156/191 |
| 5,097,783 | 3/1992 | Linville | 114/103 |
| 5,151,314 | 9/1992 | Brown | 428/198 |
| 5,162,148 | 11/1992 | Boye et al. | 428/287 |
| 5,167,897 | 12/1992 | Weber et al. | 264/288.8 |
| 5,208,098 | 5/1993 | Stover | 428/284 |
| 5,221,569 | 6/1993 | Rohrka et al. | 428/215 |
| 5,226,992 | 7/1993 | Morman | 156/62.4 |
| 5,266,390 | 11/1993 | Garland | 428/216 |
| 5,382,312 | 1/1995 | Raterman | 156/500 |
| 5,399,174 | 3/1995 | Yeo et al. | 604/365 |
| 5,409,761 | 4/1995 | Langley | 428/198 |
| 5,418,045 | 5/1995 | Pike et al. | 428/198 |
| 5,421,941 | 6/1995 | Allen et al. | 156/244.11 |
| 5,422,172 | 6/1995 | Wu | 428/230 |
| 5,429,629 | 7/1995 | Latimer et al. | 604/378 |
| 5,455,074 | 10/1995 | Nohr et al. | 427/386 |
| 5,620,788 | 4/1997 | Garavaglia et al. | 442/118 |

FILM-NONWOVEN LAMINATE CONTAINING AN ADHESIVELY-REINFORCED STRETCH-THINNED FILM

This application claims priority from U.S. Provisional Application No. 60/021,733 filed Jul. 15,1996.

FIELD OF THE INVENTION

The present invention is directed to the use of oriented, low gauge breathable films in film-nonwoven laminates.

BACKGROUND OF THE INVENTION

Film-nonwoven laminates are used in a wide variety of applications, including outer covers for personal care absorbent articles, such as diapers, training pants, incontinence garments, feminine hygiene products, sanitary napkins, wound dressings, bandages and the like. Film-nonwoven laminates also have been found useful in the health care area in such products as surgical drapes and gowns, clean room apparel, and sterilization wrappers, as well as in roll goods, such as tent material and covers for furniture, automobiles and other vehicles.

Particularly in the field of personal care absorbent articles, an emphasis has been placed on development of low cost film-nonwoven laminates that form an effective barrier to passage of body exudates (liquids and other waste matter), while exhibiting good aesthetic and tactile properties, such as hand and feel. One technique employed in attempting to achieve a satisfactory, low cost film-nonwoven laminate has been to use films of increasingly lesser gauge or thickness. Thinner films typically are lower in cost, and due to the reduced gauge, often have increased softness and are quieter during use. Such lower gauge films also can be rendered breathable or microporous more easily.

Such thin films can have an effective gauge or thickness of 0.6 mil or less and a basis weight of 25.0 grams per square meter (gsm) or less. Particularly when such low gauge films are achieved by drawing or stretching, such as in the machine direction, the drawing or stretching orients the molecular structure of the polymer molecules within the film in the direction of stretching, thereby increasing the strength of the film in the machine direction. However, the same machine direction oriented film is weakened in the cross direction in terms of tensile strength and trap tear properties.

In order to compensate for structural weaknesses in such uni-directionally stretched films, a support layer (or multiple support layers), such as a fibrous nonwoven web, has been laminated to the film layer to form a laminate having, among other properties, increased strength and durability. Laminates of stretch-thinned films and nonwovens have been formed using thermal lamination techniques, in which heat and pressure, as with heated pattern rolls and ultrasonics, have been employed. Thermal lamination of films and nonwovens requires, however, that the polymeric materials used in forming the film and nonwoven be thermally compatible, that is, the polymers can be thermally bonded to deliver a peel force of 20 grams or greater. Thus, thermal lamination techniques limit the freedom to select film and/or nonwoven polymers based solely upon cost, processability and/or performance criteria. In addition, even thermally compatible polymers may require a level of heat and pressure that results in undesired perforations in or localized film damage to the film layer, and/or in the resultant laminate being undesirably stiff. Finally, such thermally laminated film-nonwoven laminates have in some instances, particularly when employed as an outer cover for personal care absorbent articles, exhibited insufficient strength and durability properties, resulting in catastrophic tear failures of the film layer of the laminate during use of such absorbent articles. The inventors have observed that in such thermally laminated film-nonwoven laminates, tear failures of thermally laminated film-nonwoven laminates tend to propagate from thermal bond points or areas in which the film and nonwoven layers are bonded together. Accordingly, the need exists for film-nonwoven laminates incorporating an improved uniaxially (i.e., machine direction) oriented, low gauge film having enhanced strength and durability properties, particularly in the cross machine direction.

SUMMARY OF THE INVENTION

It is an object, therefore, of the present invention to provide an improved film-nonwoven laminate by adhesively laminating a uniaxially oriented, low gauge film, having enhanced strength and durability properties due to application to a surface thereof a pattern or network of adhesive areas, to a fibrous nonwoven layer.

It is another object of the present invention to provide a low cost adhesively bonded film-nonwoven laminate having enhanced strength and durability properties, and that is highly breathable.

It is still another object of the present invention to provide an improved adhesively bonded film-nonwoven laminate that avoids the need for thermal compatibility of the polymeric materials forming the film and nonwoven layers of the laminate.

These and other objects are achieved by the adhesively-reinforced film-nonwoven laminate of independent claim 1, which comprises:

a fibrous nonwoven layer having a surface;

a film layer having a surface;

said film layer being oriented in a direction of stretching and having an effective gauge of 0.6 mil or less;

said film layer being formed from a blend including, on a total weight percent basis based upon the total weight of the film layer, from about 30 percent to about 70 percent of a first polyolefin polymer, from about 70 percent to about 30 percent of a filler, and from about 0 to about 20 percent of a second polyolefin polymer;

said film layer having a water vapor transmission rate of at least about 300 grams per square meter per 24 hours;

a pattern of adhesive areas applied to said surface of said film layer;

said pattern of adhesive areas having an add-on amount of from about 0.1 to about 20 grams per square meter (gsm), a percent bond area of from about 5 percent to about 50 percent per unit area of said surface of said film layer, and a maximum spacing between adhesive areas in a direction generally parallel to said direction of stretching of about 1.0 inch or less;

said surface of said fibrous nonwoven layer being adhered to said surface of said film layer by said pattern of adhesive areas applied to said film layer surface to form a laminate.

Other advantageous features, aspects and details of the present invention are evident from the dependent claims, the description and the drawings herein. The claims herein are intended to be understood as a first non-limiting approach to defining the present invention in general terms.

DETAILED DESCRIPTION OF THE PRESENT INVENTION

The present invention is directed to an improved film-nonwoven laminate which utilizes a pattern or network of adhesive areas applied to a surface of the film layer of the laminate to improve durability and strength of the uniaxially oriented, typically machine direction, film and the film-nonwoven laminate incorporating such film. For purposes of illustration only, the present invention will be described in conjunction with its use as an outer cover material for personal care absorbent articles, which include diapers, training pants, incontinence garments, sanitary napkins, bandages and the like. As such, the invention should not be limited to these specific uses, as it is instead intended that the present invention be used in all applications in which such adhesively-reinforced film-nonwoven laminates can be suitably employed.

Figure 1:
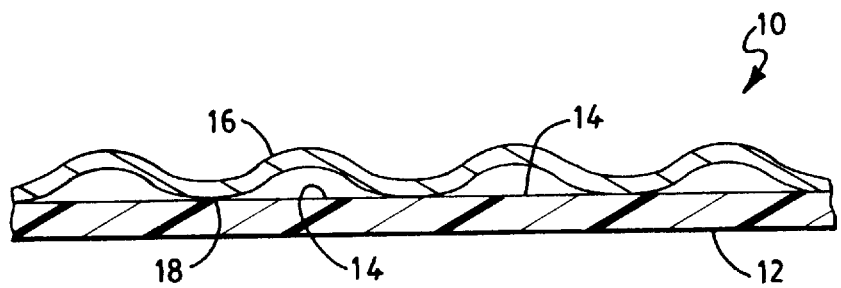
FIG. 1 is a cross-sectional view of an adhesively-reinforced breathable, cloth-like film-nonwoven laminate according to the present invention.

Referring to FIG. 1, an embodiment of the adhesively-reinforced film-nonwoven laminate of the present invention is illustrated. The adhesively-reinforced film-nonwoven laminate 10 comprises a uniaxially oriented, low gauge film layer 12 to which a nonwoven web or layer 16 is attached by a pattern or network of adhesive fibers, filaments, lines or areas 18. Adhesive areas 18 have a percent bond area of from about 5 percent to about 50 percent per unit area of the surface 14 of film layer 12 to which the adhesive areas 18 are applied and have a maximum spacing between adhesive areas in a direction generally parallel to the direction of stretching (orientation) of no more than about 1.0 inch (about 25.4 millimeters (mm)). The adhesive 18 is applied to a surface 14 of the film layer 12 adjacent the nonwoven web or layer 16 at an add-on amount ranging from about 0.1 to about 20 grams per square meter (gsm). While this is the most rudimentary execution of the present invention, further refinements and additions can be made. For example, additional layers of material may be added to the laminate 10 to form multi-layered laminates. Such additional layers of material include a second fibrous nonwoven web or layer that is bonded to a surface of film layer 12 opposite the first fibrous nonwoven web or layer 16. Alternatively, the nonwoven fabric or web 16 to which the film layer 12 is adhesively bonded may itself comprise a multi-layered nonwoven laminate or composite.

As used herein, the terms "layer" or "web" when used in the singular can have the dual meaning of a single element or a plurality of elements. As used herein, the term "laminate" means a composite material made from two or more layers or webs of material which have been attached or bonded to one another. As used herein, the terms "nonwoven fabric" or "nonwoven web" mean a web having a structure of individual fibers or filaments that are interlaid, but not in an identifiable, repeating manner as in a knitted or woven fabric. It should be noted, however, that although the present invention will be described in the context of nonwoven fabrics and webs, woven and/or knitted fabrics formed of appropriate materials can be suitably employed as a fibrous support layer of the laminate disclosed herein. As used herein, the term "machine direction" or MD means the length of a material or fabric in the direction in which it is produced. The term "cross machine direction" or CD means the width of a material or fabric, i.e., a direction generally perpendicular to the MD.

Commercially available thermoplastic polymeric materials can be advantageously employed in making the fibers or filaments from which nonwoven layer 16 is formed. As used herein, the term "polymer" shall include, but is not limited to, homopolymers, copolymers, such as, for example, block, graft, random and alternating copolymers, terpolymers, etc., and blends and modifications thereof. Moreover, unless otherwise specifically limited, the term "polymer" shall include all possible geometric configurations of the material, including, without limitation, isotactic, syndiotactic, random, and atactic symmetries. As used herein, the terms "thermoplastic polymer" or "thermoplastic polymeric material" refer to a long-chain polymer that softens when exposed to heat and returns to the solid state when cooled to ambient temperature. Exemplary thermoplastic materials include, without limitation, polyvinyl chlorides, polyesters, polyamides, polyfluorocarbons, polyolefins, polyurethanes, polystyrenes, polyvinyl alcohols, caprolactams, and copolymers of the foregoing. The fibers used in making nonwoven layer 16 may have any suitable morphology and may include hollow or solid fibers, straight or crimped fibers, bicomponent, multi-component, biconstituent or multi-constituent fibers, and blends or mixes of such fibers, as are well known in the art. Fiber lengths may be short, as in staple fibers, or substantially continuous, as in spunbond filaments. Fiber thicknesses may be adjusted to achieve desired properties suitable for the end-use application. For example, in personal care absorbent articles, average fiber diameters will typically range from about 10 microns to about 30 microns.

Nonwoven webs that can be employed as the nonwoven layer 16 of the present invention can be formed by a variety of known forming processes, including spunbonding, airlaying, meltblowing, or bonded carded web formation processes. Spunbond nonwoven webs are made from melt-spun filaments. As used herein, the term "melt-spun filaments" refers to small diameter fibers and/or filaments which are formed by extruding a molten thermoplastic material as filaments from a plurality of fine, usually circular, capillaries of a spinnerette with the diameter of the extruded filaments then being rapidly reduced, for example, by non-eductive or eductive fluid-drawing or other well known spunbonding mechanisms. Lastly, the melt-spun filaments are deposited in a substantially random manner onto a moving carrier belt or the like to form a web of substantially continuous and randomly arranged, melt-spun filaments. Spunbond filaments generally are not tacky when they are deposited onto the collecting surface. The production of spunbond nonwoven webs is described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, U.S. Pat. No. 3,276,944 to Levy, U.S. Pat. No. 3,502,538 to Peterson, and U.S. Pat. No. 3,542,615 to Dobo et al., all of which are incorporated herein by reference. The melt-spun filaments formed by the spunbond process are generally continuous and have average diameters larger than 7 microns based upon at least 5 measurements, and more particularly, between about 10 and 100 microns. Another frequently used expression of fiber or filament diameter is denier, which is defined as grams per 9000 meters of a fiber or filament.

The spunbond process also can be used to form bicomponent spunbond nonwoven webs as, for example, from side-by-side or sheath-core linear low density polyethylene/polypropylene spunbond bicomponent filaments. A suitable process for forming such bicomponent spunbond nonwoven webs is described in U.S. Pat. No. 5,418,045 to Pike et al., which is incorporated herein by reference in its entirety. Briefly, this process for forming such bicomponent filaments and resultant webs includes using a pair of extruders for separately supplying both the polymeric components to a bicomponent spinnerette. Spinnerettes for producing bicomponent filaments are well known in the art and, therefore, are not described in detail herein. Generally, the spinnerette includes a housing containing a spin pack, which includes a plurality of vertically stacked plates having a pattern of openings arranged to create flow paths for directing the high melting temperature and low melting temperature polymers separately to the fiber-forming openings in the spinnerette. The spinnerette has openings arranged in one or more rows and the openings form a downwardly extending curtain of filaments when the polymers are extruded through the spinnerette. As the curtain of filaments exit the spinnerette, they are contacted by a quenching gas from one or both sides of the filament curtain, which at least partially quenches the filaments and develops a latent helical crimp in the filaments extending from the spinnerette. Typically, the quenching air will be directed generally perpendicularly to the length of the filaments at a velocity of from about 30 to about 120 meters per minute and at a temperature of about 7 degrees Celsius (° C.) to about 32° C.

A fiber draw unit or aspirator is positioned below the spinnerette to receive the quenched filaments. Fiber draw units or aspirators for use in melt spinning polymers are well known in the art. Exemplary fiber draw units suitable for use in this process include a linear fiber aspirator of the type shown in U.S. Pat. No. 3,802,817 to Matsuki et al., and eductive guns of the type shown in U.S. Pat. Nos. 3,692,618 to Dorschner et al. and 3,423,266 to Davies et al., the disclosures of which are incorporated herein by reference in their entirety. The fiber draw unit in general has an elongate passage through which the filaments are drawn by aspirating gas flowing through the passage. The aspirating gas may be any gas, such as air, that does not adversely interact with the polymers of the filaments. A heater of conventional construction supplies hot aspirating gas to the fiber draw unit. As the aspirating gas draws the quenched filaments and ambient air through the fiber draw unit, the filaments are heated to a temperature that is required to activate the latent crimping therein. The temperature required to activate the latent crimping within the filaments typically will range from about 43° C. to a maximum of less than the melting point of the low melting component polymer. Generally, a higher air temperature produces a higher number of crimps per unit length of the filament. Alternatively, the curtain of filaments exiting the spinnerette may be drawn at ambient temperature, consequently forming a web of substantially straight or non-crimped spunbond filaments.

The drawn and crimped filaments exit the fiber draw unit and are deposited onto a continuous forming surface in a random manner, generally assisted by a vacuum device placed underneath the forming surface. The purpose of the vacuum is to eliminate the undesirable scattering of the filaments and to guide the filaments onto the forming surface to form a uniform unbonded nonwoven web of bicomponent filaments. If desired, the resultant bicomponent spunbond web can be subjected to pre-bonding or secondary bonding, as described below.

Spunbond webs generally are stabilized or consolidated (pre-bonded) in some manner immediately as they are produced in order to give the web sufficient integrity and strength to withstand the rigors of further processing into a finished product. This pre-bonding step may be accomplished through the use of an adhesive applied to the filaments as a liquid or powder which may be heat activated, or more commonly, by compaction rolls. As used here, the term "compaction rolls" means a set of rollers above and below the nonwoven web used to compact the web as a way of treating a just produced, melt-spun filament, particularly spunbond, web, in order to give the web sufficient integrity for further processing, but not the relatively strong bonding of later applied, secondary bonding processes, such as through-air bonding, thermal bonding, ultrasonic bonding and the like. Compaction rolls slightly squeeze the web in order to increase its self-adherence and thereby its integrity.

An exemplary secondary bonding process utilizes a patterned roller arrangement for thermally bonding the spunbond web. The roller arrangement typically includes a patterned bonding roll and smooth anvil roll which together define a thermal patterning bonding nip. Alternatively, the anvil roll may also bear a bonding pattern on its outer surface. The pattern roll is heated to a suitable bonding temperature by conventional heating means and is rotated by conventional drive means, so that when the spunbond web passes through the nip, a series of thermal pattern bonds is formed. Nip pressure within the nip should be sufficient to achieve the desired degree of bonding of the web, given the line speed, bonding temperature and materials forming the web. Percent bond areas within the range of from about 10 percent to about 20 percent are typical for such spunbond webs.

Meltblown fibers are formed by extruding molten thermoplastic material through a plurality of fine, usually circular, die capillaries as molten threads or filaments into opposing flows of high velocity, usually heated, gas streams, such as air, which attenuate the filaments of molten thermoplastic material to reduce their diameters and break the streams into discontinuous fibers of small diameter. Thereafter, the meltblown fibers are deposited onto a collecting surface to form a web of randomly dispersed meltblown fibers. The meltblown web possesses integrity due to entanglement of individual fibers in the web as well as some degree of thermal or self-bonding between the fibers, particularly when collection is effected only a short distance after extrusion. The meltblown process is well-known and is described in various patents and publications, including NRL Report 4364, "Manufacture of Super-Fine Organic Fibers" by B. A. Wendt, E. L. Boone and C. D. Fluharty; NRL Report 5265, "An Improved Device for the Formation of Super-Fine Thermoplastic Fibers" by K. D. Lawrence, R. T. Lukas, and J. A. Young; U.S. Pat. No. 3,676,242, to Prentice; U.S. Pat. No. 3,849,241 to Buntin et al.; and U.S. Pat. No. 4,720,252 to Appel et al.; the disclosures of which all are incorporated herein by reference in their entirety. In general, meltblown fibers contained in meltblown webs have an average fiber diameter of up to about 10 microns with very few, if any, of the fibers exceeding 10 microns in diameter. Usually, the average diameter of the fibers in such meltblown webs is about 2–6 microns. While the fibers in meltblown webs are predominately discontinuous, such fibers generally have a length exceeding that normally associated with staple fibers.

Suitable nonwoven webs for use in making the present invention also may be made from bonded carded webs and airlaid webs. Bonded carded webs are made from staple fibers, which usually are purchased in bales. The bales are placed in a picker, which separates the fibers. Then, the fibers are sent through a combing or carding unit, which further breaks apart and aligns the staple fibers in the machine direction to form a generally machine direction oriented fibrous nonwoven web. Once the web is formed, it may be bonded as described herein.

Airlaying is another well known process by which fibrous nonwoven webs can be formed. In the airlaying process, bundles of small fibers having typical lengths ranging from about 6 to about 19 millimeters (mm) are separated and entrained in an air supply and then deposited onto a forming screen, usually with the assistance of a vacuum supply. The randomly deposited fibers then can be bonded to one another using known bonding techniques.

It is also possible to form laminates for use as the fibrous nonwoven layer 16 in the present invention. Such laminates include spunbond/meltblown laminates and spunbond/meltblown/spunbond laminates as are taught, for example, in U.S. Pat. No. 4,041,203 to Brock et al., the disclosure of which is incorporated herein by reference in its entirety. With spunbond/meltblown laminates, it is generally more desirable to attach the meltblown portion of the laminate to the film layer. In addition, in certain applications, it may be desirable to add additional layers to the film-nonwoven laminate such as, for example, a second nonwoven or other support layer to the surface of the film layer that is opposite that of the first or other nonwoven layer. Here again, the second support layer may be, for example, a single layer of nonwoven material or a laminate, as described herein.

Film layer 12 includes at least two basic components: a polyolefin polymer, advantageously a predominately linear polyolefin polymer, such as linear low density polyethylene (LLDPE) or polypropylene, and a filler. These components are mixed together, heated and then extruded into a film layer using any one of a variety of film-producing processes known to those of ordinary skill in the film processing art. Such film-making processes include, for example, cast embossed, chill and flat cast, and blown film processes. Other additives and ingredients may be added to the film layer 12 provided they do not significantly interfere with the ability of the film layer to function in accordance with the teachings of the present invention.

Generally, on a dry weight basis, based on the total weight of the film, the film layer 12 will include from about 30 to about 70 weight percent of the polyolefin polymer, and from about 30 to about 70 weight percent of the filler. In more specific embodiments, it may include in addition from about 0 to about 20 percent by weight of another polyolefin polymer, such as low density polyethylene.

Linear low density polyethylene has been found to work well as a film base when blended with appropriate amounts of a filler. It is believed, however, that any suitable polyolefin polymer can be used in forming the film layer 12 of the present invention, and advantageously any predominately linear polyolefin polymer can be used in forming the film layer 12 of the present invention. As used herein, the term "linear low density polyethylene" is meant to include polymers of ethylene and higher alpha olefin comonomers such as $C_3$–$C_{12}$ and combinations thereof and has a Melt Index (MI) as measured by ASTM D-1238 Method D of from about 0.5 to about 10 (grams per 10 minutes at 190° C.). By "predominately linear" it is meant that the main polymer chain is linear with less than approximately 5 long chain branches per 1000 ethylene units. Long chain branches would include carbon chains greater than $C_{12}$. For predominately linear polyolefin polymers that are nonelastic, short chain branching ($C_3$–$C_{12}$) due to comonomer inclusion will typically be limited to less than 20 short chains per 1000 ethylene units and 20 or greater for polymers which are elastomeric. Examples of predominately linear polyolefin polymers include, without limitation, polymers produced from the following monomers: ethylene, propylene, 1-butene, 4-methyl-pentene, 1-hexene, 1-octene and higher olefins as well as copolymers and terpolymers of the foregoing. In addition, copolymers of ethylene and other olefins including butene, 4-methyl-pentene, hexene, heptene, octene, decene, etc., would also be examples of predominately linear polyolefin polymers.

In addition to the polyolefin polymer, the film layer 12 also includes a filler. As used herein, a "filler" is meant to include particulates and other forms of materials which can be added to the film polymer extrusion blend and which will not chemically interfere with the extruded film but which are able to be uniformly dispersed throughout the film. Generally, the fillers will be in particulate form and may have a spherical or non-spherical shape with average particle sizes in the range of about 0.1 to about 7 microns. Both organic and inorganic fillers are contemplated to be within the scope of the present invention provided that they do not interfere with the film formation process, or the ability of the film layer to function in accordance with the teachings of the present invention. Examples of suitable fillers include calcium carbonate ($CaCO_3$), various kinds of clay, silica ($SiO_2$), alumina, barium carbonate, sodium carbonate, magnesium carbonate, talc, barium sulfate, magnesium sulfate, aluminum sulfate, titanium dioxide ($TiO_2$), zeolites, cellulose-type powders, kaolin, mica, carbon, calcium oxide, magnesium oxide, aluminum hydroxide, pulp powder, wood powder, cellulose derivatives, chitin and chitin derivatives. A suitable coating, such as, for example, stearic acid, may also be applied to the filler particles, as desired.

As mentioned herein, film layer 12 may be formed using any one of the conventional processes known to those familiar with film formation. The polyolefin polymer and filler are mixed in appropriate proportions given the ranges outlined herein and then heated and extruded into a film. In order to provide uniform breathability as reflected by the water vapor transmission rate of the film, the filler should be uniformly dispersed throughout the polymer blend and, consequently, throughout the film layer itself. For purposes of the present invention, a film is considered "breathable" if it has a water vapor transmission rate of at least 300 grams per square meter per 24 hours ($g/m^2/24$ hrs) as calculated using the test method described herein. Generally, once the film is formed, it will have a weight per unit area of less than about 80 grams per square meter (gsm) and after stretching and thinning, its weight per unit area will be from about 12 grams per square meter to about 25 grams per square meter.

The film layers used in the examples of the present invention described below were monolayer films, however, other types, such as multi-layer films, are also considered to be within the scope of the present invention provided the forming technique is compatible with filled films. The film as initially formed is generally thicker and noisier than desired, as it tends to make a "rattling" sound when shaken. Moreover, the film does not have a sufficient degree of breathability as measured by its water vapor transmission rate. Consequently, the film is heated to a temperature equal to or less than about 5° C. below the melting point of the polyolefin polymer and then stretched using an in-line machine direction orientation (MDO) unit to at least about two times (2×) its original length to thin the film and render it porous. Further stretching of the film layer 12, to about three times (3×), four times (4×), or more, its original length is expressly contemplated in connection with forming film layer 12 of the present invention.

Film layer 12 after being stretch-thinned should have an "effective" film gauge or thickness of from about 0.2 mil to about 0.6 mil. The effective gauge is used to take into consideration the voids or air spaces in breathable film layers. For normal, non-filled, non-breathable films, the actual gauge and effective gauge of the film will typically be the same. However, for filled films that have been stretch-thinned, as described herein, the thickness of the film will also include air spaces. In order to disregard this added volume, the effective thickness is calculated according to the test method set forth herein.

An additional feature of the stretch-thinning process is the change in opacity of the film material. As formed, the film is relatively transparent, however, after stretching the film becomes opaque. In addition, while the film becomes oriented during the stretch-thinning process, it also becomes softer and the degree of "rattling" is reduced.

Such uniaxially, machine direction oriented films typically do not have good strength properties in the cross machine direction, resulting in films that are easily torn or split along the machine direction (the direction of stretching). One approach to resolving the problem of "splittiness" in such stretch-thinned films has been to thermally bond the film layer to a fibrous nonwoven web or layer, with the latter fibrous support layer reinforcing the film and, for the most part, determining the durability and strength properties of the resulting film-nonwoven laminate. As noted herein, however, such thermally-bonded film-nonwoven laminates exhibit certain deficiencies, particularly when incorporating machine direction oriented filled films stretched up to four times their original length to render the film microporous or breathable.

The adhesively reinforced film-nonwoven of the present invention, as compared to thermally bonded film-nonwoven laminates, allows thermally incompatible films and nonwoven webs, such as LLDPE films and polypropylene nonwoven webs, to be effectively laminated. The resulting laminate has excellent aesthetic qualities, such as hand and feel, lamination strength, durability and strength properties, and is highly breathable, without undesirable weak points or perforations in the film layer caused by excessive heat and/or pressure when thermally bonded.

The term "adhesive" as used herein is intended to refer to any suitable hot melt, water or solvent borne adhesive that can be applied to a surface 14 of the film layer 12 in the required pattern or network of adhesive areas 18 to form the film-nonwoven laminate of the present invention. Accordingly, suitable adhesives include conventional hot melt adhesives, pressure-sensitive adhesives and reactive adhesives (i.e., polyurethane). More specifically, block copolymer-type construction adhesives, ethylene vinyl acetate (EVA)-based adhesives (e.g., 18–30 weight percent vinyl acetate) and amorphous alphaolefin copolymer and terpolymer-based adhesives have been found to work well in forming the film-nonwoven laminate of the present invention. All such adhesive types can be formulated to contain waxes and tackifiers to improve processing or hot tack or softness.

The adhesive application process employed must be suited to the particular type of adhesive used, such that the film layer and nonwoven layer are adhesively bonded to yield a peel strength of 20 grams or more. The adhesive can be applied, for example, in a pattern or network of intersecting, randomly dispersed meltblown adhesive fibers. Such meltblown adhesive fibers typically have average diameters in the range of from about 5 microns to about 50 microns. As used herein, the term "meltblown adhesive fibers" is intended to include both discontinuous and continuous adhesive fibers. Processes for applying meltblown fibers onto the surface of a moving substrate are known, as exemplified by U.S. Pat. No. 4,720,252 to Appel et al., the disclosure of which is incorporated herein by reference.

Figure 3:
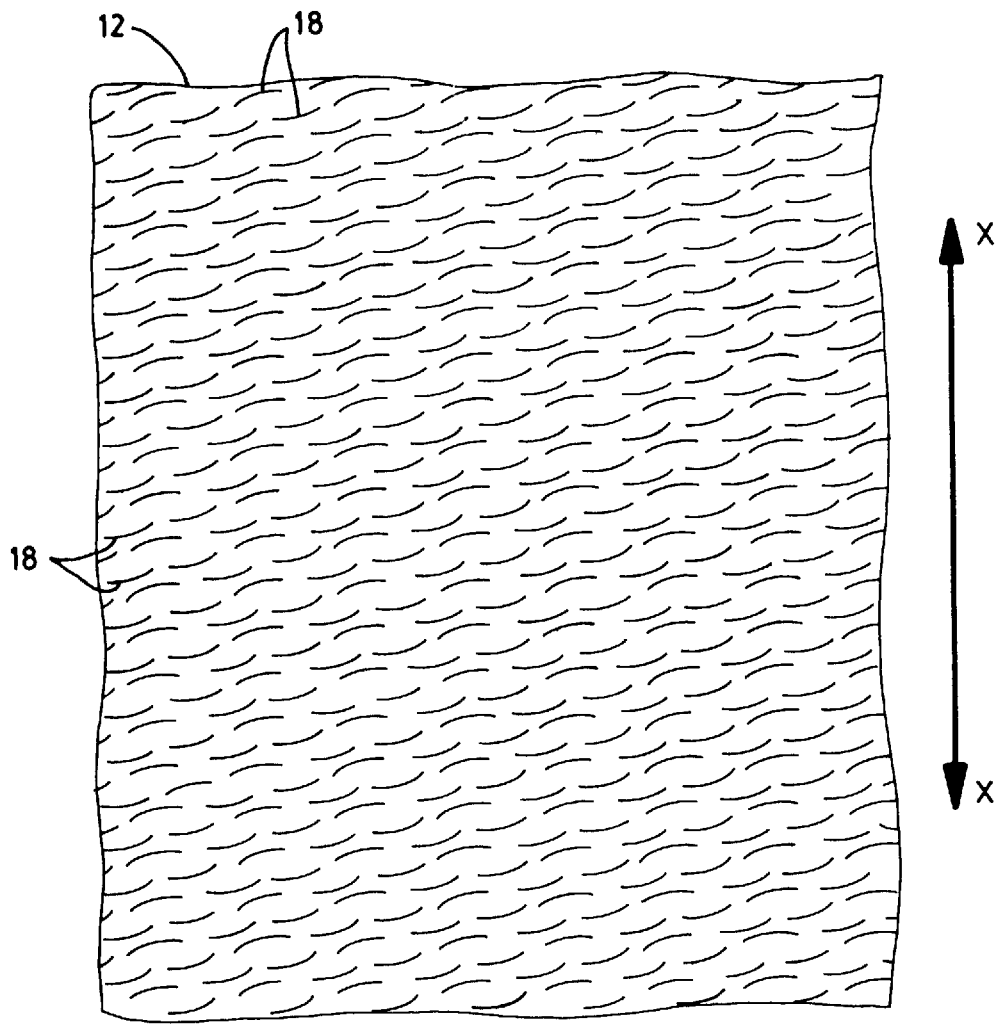
FIG. 3 is an elevational view of a ribbed pattern of printed pigmented adhesive areas applied to a surface of a film layer according to the present invention, in which the direction of stretching of the film layer is indicated by line x—x.
Figure 2:
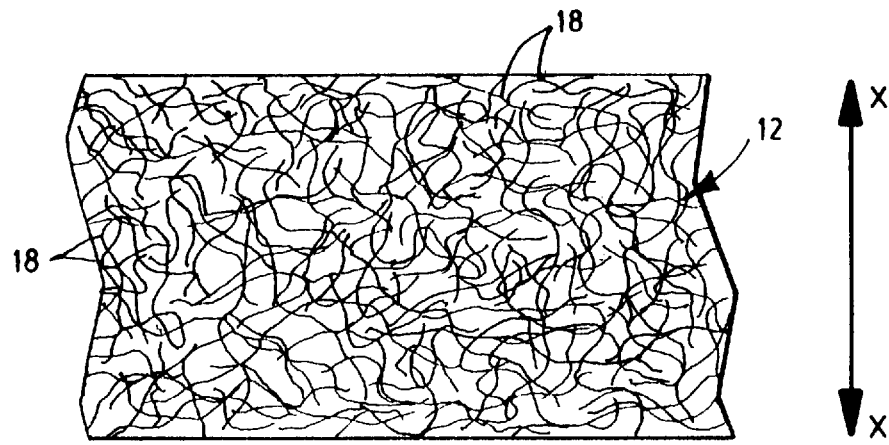
FIG. 2 is an elevational view of a random pattern of meltblown adhesive fibers applied to a surface of a film layer according to the present invention, in which the direction of stretching of the film layer is indicated by line x—x.
Figure 4:
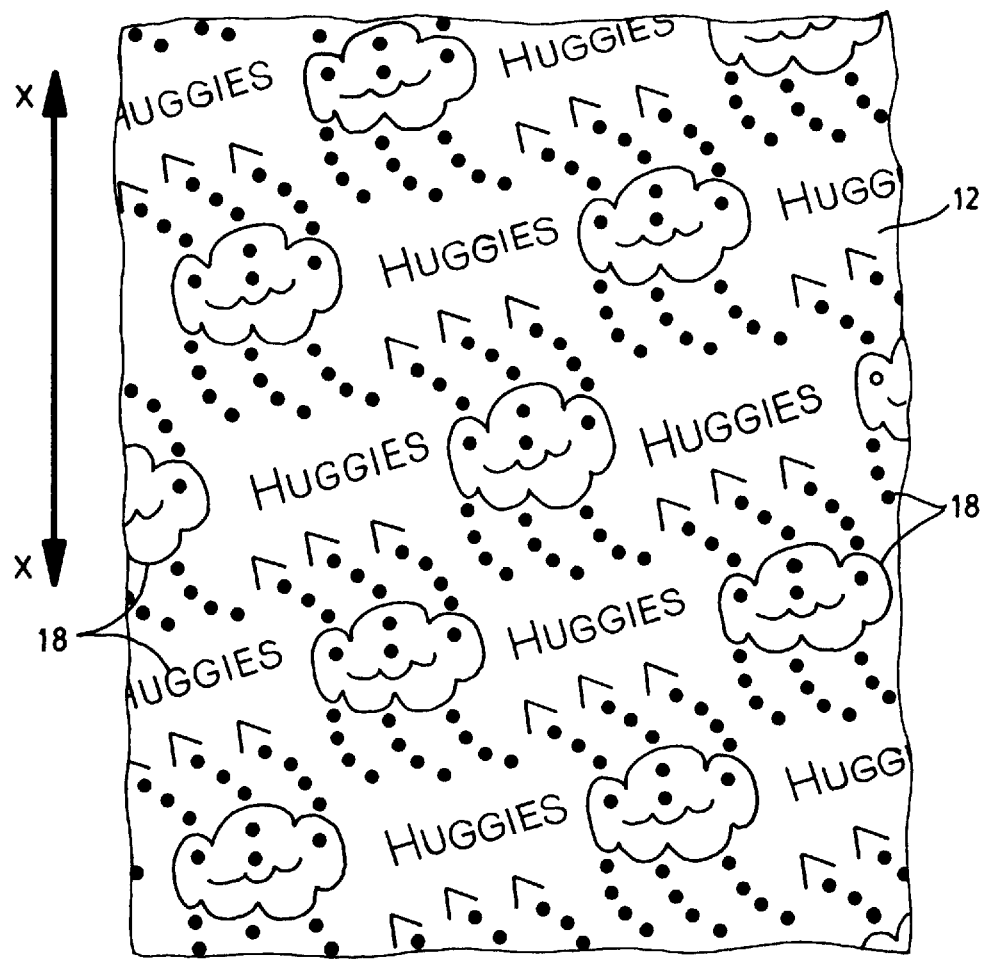
FIG. 4 is an elevational view of a cloud pattern of printed pigmented adhesive areas applied to a surface of a film layer according to the present invention, in which the direction of stretching of the film layer is indicated by line x—x.

Other suitable processes for applying adhesive to the film layer 12 include, for example, sprayed or swirled hot melt adhesive areas, and screen or gravure printing of adhesive areas. Such melt spraying and adhesive printing processes are well known in the art and are, therefore, not described in detail herein. Application of adhesives, particularly pigmented adhesives, using such printing processes offers additional aesthetic benefits, as the adhesive pattern can be in the form of geometric or non-geometric and repeating or non-repeating shapes, continuous or discontinuous lines, fanciful or arbitrary designs, symbols or objects, or even text or words. The adhesive patterns shown in FIGS. 3 and 4 are illustrative of such printed adhesive patterns.

Certain printing processes, such as screen printing, require direct contact between the screen and the substrate being printed. Printing certain types of adhesives, such as some pressure sensitive adhesives, can prove problematic due to the high tack or level of adhesion of such adhesives at ambient temperature. Screen printing of such adhesives can be accomplished, however, by printing the adhesive onto a suitable release surface, such as, for example, a release paper, and then transferring the printed adhesive onto the film layer 12 from the release surface, before bonding the film layer 12 to nonwoven layer 16.

Irrespective of the particular adhesive application process employed in forming the adhesively reinforced film-nonwoven laminate of the present invention, the inventors have found that the adhesive must be applied to a surface of the film layer 12, directly or indirectly, rather than to the nonwoven layer 16. When applied to a surface of the nonwoven layer 16, due to the fibrous nature of nonwoven web, the uniformity of adhesive available for reinforcement of film layer 12 is decreased. Adhesive can penetrate into and through the interstices between individual fibers of the nonwoven layer 16, thereby reducing the continuity of adhesive available to reinforce film layer 12. Particularly with respect to screen or pattern printed adhesives, application of adhesive onto the nonwoven layer results in a poor pattern definition, lessening the aesthetic benefits of adhesive printing processes referred to herein. By applying the adhesive 18 to surface 14 of film layer 12, the amount of adhesive available for film layer reinforcement, and the adhesive application pattern, can be effectively controlled. Moreover, application of adhesive 18 should be substantially coextensive with the length and width of film layer 12, in order to ensure uniformity in strength and durability properties of the adhesively-reinforced film-nonwoven laminate utilizing such film layer 12, and to reduce delamination of the film layer 12 and nonwoven layer 16 during use of film-nonwoven laminate 10.

A primary function of the adhesive areas is to reinforce the low gauge or stretch-thinned film layer of the film-nonwoven laminate. As noted herein, films that are highly oriented (2x or more) in the machine direction (MD) tend to be "splitty" in the machine direction when subjected to cross machine direction (CD) tensile forces. The inventors have observed that a randomly dispersed, intersecting network of meltblown adhesive areas applied to such a film in accordance with the present invention works particularly well in providing a "rip-stop" against such film splitting by distributing CD tensile loads applied to the film, thereby enhancing the durability and strength of such machine direction oriented films, and the film-nonwoven laminates incorporating such films. More specifically, the network of randomly dispersed, intersecting meltblown adhesive areas includes individual meltblown adhesive fibers that are "closely spaced" in the MD. As used herein, the term "closely spaced adhesive areas" refers to adhesive areas that are separated by a maximum distance between individual adhesive areas of about 1.0 inch (25.4 mm) in a direction generally parallel to the direction of stretching, and more specifically a maximum distance of 0.25 inch (6.35 mm), and even more specifically a maximum distance of 0.125 inch (3.18 mm). As used herein, the term "generally parallel to the direction of stretching" means a line along which the distance between adhesive areas is measured will have an interior angle with a line in the direction of stretching of less than or equal to 30°. By limiting the maximum spacing between individual adhesive areas in the direction of stretching of the film layer, for example, the machine direction, to the specified range, the formation and propagation of holes or tears in film layer 12 is reduced, and the amount of elongation in the cross machine direction the film layer 12 can withstand before splitting or tearing is increased. Stated alternatively, by increasing the connectivity and proximity of individual adhesive areas within the adhesive pattern or network, splittiness of film layer 12 is effectively reduced.

Although a randomly dispersed, intersecting network of adhesive areas, such as meltblown adhesive fibers, can be effectively utilized in forming the adhesively reinforced film-nonwoven laminate of the present invention, as noted herein, other adhesive application patterns and methods can be employed as well. For example, generally parallel, continuous and/or discontinuous, adhesive lines extending or oriented in the cross machine direction and printed onto surface 14 of film layer 12 at an add-on amount and percent bond area within the ranges specified herein can impart the desired increase in strength and durability to film layer 12 to yield, when attached to nonwoven layer 16, the film-nonwoven laminate of the present invention. Use of suitable adhesive application methods is limited by their capacity to control the add-on amount of adhesive used, percent bond area of the adhesive areas, the maximum spacing between individual adhesive areas in the direction of stretching (MD), and bonding of the film layer to the nonwoven layer while the adhesive is sufficiently tacky for the film-nonwoven laminate to deliver a peel strength of 20 grams or more. The adhesive add-on amount should range from about 0.1 to about 20 grams per square meter, and more specifically from about 0.25 to about 5.0 grams per square meter, and even more specifically from about 0.5 to about 1.5 grams per square meter. Reducing the add-on amount lowers the cost of producing the film-nonwoven laminate, and reduces the risk of compromising breathability of the film layer. By way of contrast, higher add-on amounts of adhesive provide more durable film-nonwoven laminates, suitable for multi-use end products.

By applying a pattern or network of adhesive areas as described herein, as compared to a continuous coating of adhesive, for example, the microporosity or breathability of the film-nonwoven laminate is not significantly reduced. A continuous adhesive coating further is considered undesirable by the inventors for use in forming the film-nonwoven laminate of the present invention due to its effect on physical properties of the resulting laminate, such as drape and cup crush. The portion of the total area of surface 14 of the film layer 12 to which adhesive areas 18 are applied can be expressed as a percent bond area. The term "percent bond area" as used herein refers to the portion of the total plan area of surface 14 of the film layer 12 that is occupied by adhesive areas 18. The percent bond area can be measured by a variety of conventional techniques, including imaging analysis as described herein. By limiting the percent bond area of the adhesive areas to a range of from about 5 percent to about 50 percent per unit area of the surface 14 of film layer 12 to which the adhesive areas are applied, and controlling the maximum spacing of adhesive area application, as well as the adhesive add-on amount, adhesive reinforcement of low gauge, stretch-thinned breathable filled films used in forming film-nonwoven laminates can be accomplished without adversely impacting the breathability of the resulting laminate.

Although the adhesively-reinforced film-nonwoven laminate of the present invention has been described herein as incorporating a uniaxially oriented or stretched film layer, the benefits and advantages of the present invention can apply to biaxially oriented or stretched films as well. Likewise, although application of adhesive areas 18 to a surface 14 of the film layer 12 has been described herein, adhesive areas also can be applied to a surface opposing surface 14 of the film layer 12, wherein adhesive areas on the opposing surfaces of film layer 12 are identical or different in terms of add-on amount, percent bond area and maximum spacing in the direction of stretching.

Figure 5:
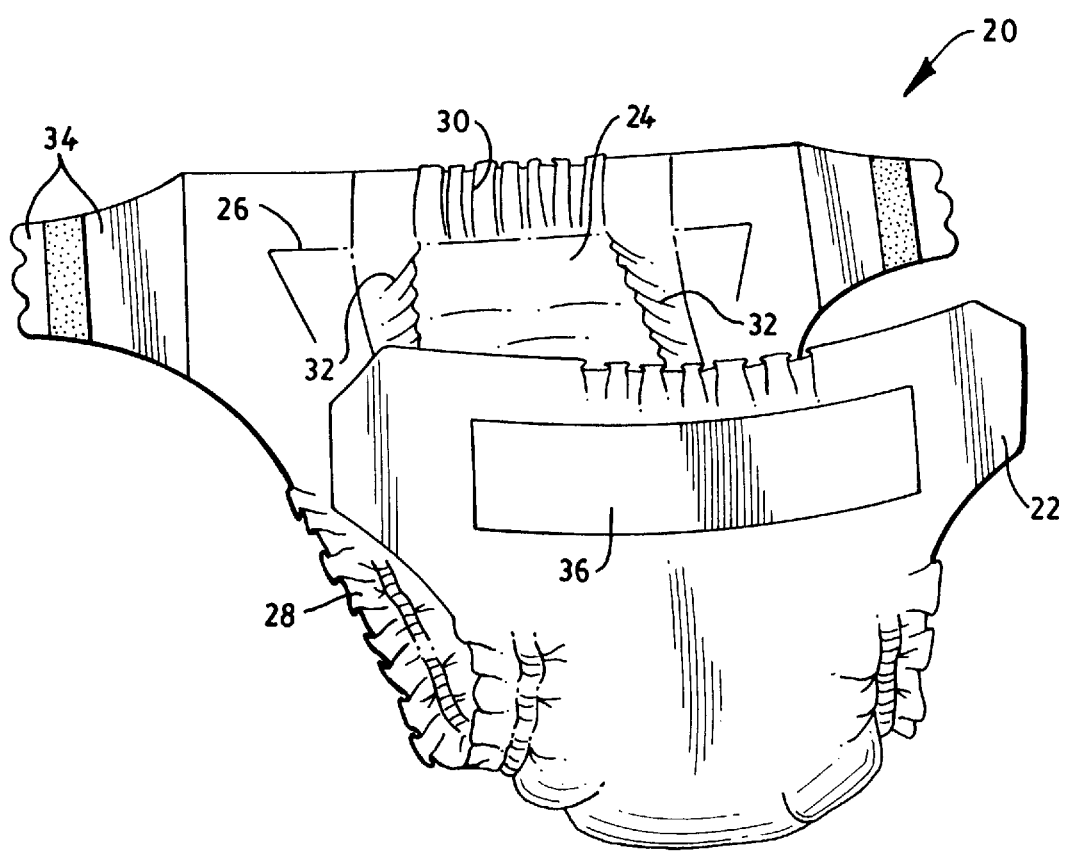
FIG. 5 is a perspective view of a disposable diaper with the adhesively-reinforced film-nonwoven laminate of the present invention as an outer cover.

The adhesively-reinforced film-nonwoven laminate of the present invention has a wide variety of end-use applications, including an outer cover material for personal care absorbent articles, such as disposable diaper 20 shown in FIG. 5. Diaper 20, as is typical for most personal care absorbent articles, includes a liquid permeable body side liner 24 and a liquid impermeable outer cover 22, wherein outer cover 22 comprises the adhesively-reinforced film-nonwoven laminate of the present invention. Various woven, nonwoven and apertured film materials can be used for body side liner 24. For example, the body side liner may be composed of a meltblown or spunbond nonwoven web of polyolefin fibers, of a bonded carded web of natural and/or synthetic fibers.

Disposed between liner 24 and outer cover 22 is an absorbent core 26 formed, for example, of a blend of hydrophilic cellulosic woodpulp fluff fibers and highly absorbent gelling particles (e.g., superabsorbent material). Absorbent core 26 is generally compressible, conformable, and non-irritating to the wearers skin, and capable of absorbing and retaining liquid body exudates. For purposes of this invention, absorbent core 26 can comprise a single, integral piece of material, or a plurality of individual separates pieces of material. The size and absorbent capacity of absorbent core 26 should be compatible with the size of the intended user and liquid loading imparted by the intended use of the diaper 20. Suitable constructions and arrangements of diapers including such liners, outer covers and absorbent structures are described, for example, in U.S. Pat. No. 5,429,629 to Latimer et al., the disclosure of which is incorporated herein by reference in its entirety.

An elastic member may optionally be disposed adjacent each longitudinal edge 28 of diaper 20. Such elastic members are arranged to draw and hold the lateral, side margins 28 of diaper 20 against the legs of the wearer. Additionally, an elastic member also may be disposed adjacent either or both of the end edges 30 of diaper 20 to provide an elasticized waistband.

Diaper 20 may further include optional containment flaps 32 made from or attached to body side liner 24. Suitable constructions and arrangements of diapers including such containment flaps are described, for example, in U.S. Pat. No. 4,704,116 to K. Enloe, the disclosure of which is incorporated herein by reference in its entirety.

To secure the diaper 20 about the wearer, the diaper will have some type of fastening means attached thereto. As shown in FIG. 5, the fastening means is a hook and loop fastening system including hook elements 34 attached to the inner and/or outer surface of outer cover 22 in the back waistband region or diaper 20 and one or more loop elements or patches 36 attached to the outer surface of outer cover 22 in the front waist band region of diaper 20.

Having described certain specific embodiments of the present invention, a series of sample adhesively-reinforced film-nonwoven laminates were formed to further illustrate the present invention. The results of these tests, and the test procedures used, are set forth below.

TEST PROCEDURES

The following test procedures were used to analyze the sample materials described herein.

Effective Gauge

The effective gauge of a film material was calculated by dividing the basis weight of the film by the density of the polymer(s) and fillers forming the film. To obtain the effective gauge of a film material in units of inches, the weight per unit area measured in ounces per square yard (osy) was multiplied by 0.001334 (a metric to English conversion factor) and the result was divided by the density of the polymer formulation in grams per cubic centimeter (g/cc).

Tensile Strength and Elongation Tests

The strip test method for tensile strength and elongation measures the breaking load and percent elongation before rupture of a material. These measurements are made while the material is subjected to a continually increasing load in a single direction at a constant rate of extension.

For each sample film-nonwoven laminate material, 3 specimens were cut with a 3 inch (76 mm) wide precision cutter, with each having a width of 3 inches (76 mm) and length of 6 inches (152 mm), with the long dimension parallel to the direction of testing and force application. The entire width of each specimen was placed within clamps of a constant-rate-of-extension tester, such as a Sintech System 2 Computer Integrated Testing System manufactured by MTS Systems Corporation of Eden Prairie, Minn. The length or long dimension of each specimen was set as nearly parallel as possible to the direction of force application. A continuous load was applied to the specimen, with the crosshead speed set at 300 millimeters per minute, until the specimen ruptured. The peak load and peak strain required just prior to rupture of each specimen was measured and average values are recorded herein.

Water Vapor Transmission Rate

The water vapor transmission rate (WVTR) for the sample materials was calculated in accordance with ASTM Standard E96-80. Circular samples measuring three inches in diameter were cut from each of the test materials and a control, which was a piece of CELGARD® 2500 film from Hoechst Celanese Corporation of Sommerville, N.J. CELGARD® 2500 film is a microporous polypropylene film. Three samples were prepared for each material. The test dish was a number 60-1 Vapometer pan distributed by Thwing-Albert Instrument Company of Philadelphia, Penn. One hundred milliliters (ml) of distilled water was poured into each Vapometer pan and individual samples of the test materials and control material were placed across the open tops of the individual pans. Screw-on flanges were tightened to form a seal along the edges of each pan (no sealant grease is used), leaving the associated test material or control material exposed to the ambient atmosphere over a 6.5 centimeter (cm) diameter circle having an exposed area of approximately 33.17 square centimeters. The pans were weighed, then were placed in a forced air oven set at a temperature of 37° C. The oven was a constant temperature oven with external air circulating through it to prevent water vapor accumulation inside. A suitable forced air oven is, for example, a Blue M Power-O-Matic 60 oven distributed by Blue M Electric Company of Blue Island, Ill. After 24 hours, the pans were removed from the oven and weighed again. The preliminary test water vapor transmission rate values were calculated as follows:

Test $WVTR$ g/m$^2$/24 hrs=(grams weight loss over 24hours)×315.5

The relative humidity within the oven was not specifically controlled.

Under predetermined set conditions of 100° F. (32° C.) and ambient relative humidity, the WVTR for the CELGARD® 2500 film control has been determined to be 5000 grams per square meter for 24 hours. Accordingly, the control sample was run with each test and the preliminary test values were corrected to set condition using the following equation:

$WVTR$ g/m$^2$/24 hrs=(Test $WVTR$/control $WVTR$)×5000 g/m$^2$/24 hrs)

Hydrostatic Pressure Test

The hydrostatic pressure tests measures the resistance of nonwoven materials to the penetration of water under low hydrostatic pressure. This test procedure is in accordance with Method 5514—Federal Test Methods Standard No. 191A, AATCC Test Method 127-89 and INDA Test Method 80.4-92.

The test head of a Textest FX-300 Hydrostatic Head Tester, available from Schmid Corp., having offices in Spartanburg, S.C. is filled with purified water. The purified water is maintained at a temperature between 65° F. and 85° F. (18.3 and 29.4° C.), which is within the range of normal ambient conditions (about 73° F.(23° C.) and about 50% relative humidity) at which this test is conducted. An 8 inch×8 inch (20.3 cm×20.3 cm) square sample of the film-nonwoven laminate material, with the nonwoven layer oriented opposite the surface of the water in the test head, is placed such that the test head reservoir is covered completely. The sample is subjected to a standardized water pressure, increased at a constant rate until leakage is observed on the outer surface of the sample material. Water pressure is measured as the hydrostatic head height reached at the first sign of leakage in three separate areas of the sample. This test is repeated for 3 specimens of each sample film-nonwoven laminate material. The head height results for each specimen are averaged and recorded in centimeters. A higher value indicates greater resistance to water penetration.

Peel Strength

To test the bond strength between the film layer and nonwoven layer, a delamination or peel strength test was performed. Samples of the film-nonwoven laminate material measuring 102 mm by 152 mm were cut. A 102 mm by 152 mm piece of masking tape was applied to the surface of the film layer opposite the film surface bonded to the nonwoven layer to provide support to the film. The film and nonwoven layers were manually separated at one end for a distance of about 55 mm to produce edges that were be placed within the jaws of a Sintech System 2 Computer Integrated Testing System manufactured by MTS Systems Corporation of Eden Prairie, Minn. The free end of the film layer was secured in the moving, upper jaw, while the free end of the nonwoven layer was secured in the stationery, lower jaw. The jaw gap was set at a span of 100 millimeters and enough of the laminate material was left in the laminated state so that the jaws could travel 65 millimeters. The sample was positioned in the jaws so that the sample would start delaminating before the jaws expanded 10 millimeters. The crosshead speed was set at 300 millimeters per minute and the data was then recorded between the 10 mm start point and the 65 mm end point. The average peel strength in grams to delaminate the film layer from the nonwoven layer was then recorded as the bond strength, indicating the peel strength or load in grams necessary to separate the two layers. The standard index in grams with a maximum, minimum and mean value also were measured.

Cup Crush Test

The cup crush test is used to measure the softness of a material by using the peak load and energy units from a constant-rate-of-extension tensile testing machine. The lower the peak load value, the softer the material.

This test procedure was conducted in a controlled environment wherein the temperature was about 73° F. and the relative humidity was about 50 percent. Samples were tested using a Sintech System 2 Computer Integrated Testing System available from Sintech Corp, having offices in Cary, N.C., and a Crush Test Stand available from Kimberly-Clark Corporation Quality Assurance Department in Neenah, Wis., which included a model 11 foot, a model 31 steel ring, a base plate, a model 41 cup assembly, and a calibration set.

The steel ring was placed over the forming cylinder and a 9×9 inch (22.9 cm×22.9 cm) sample was centered over the forming cylinder. The forming cup was slid over the forming cylinder until the sample was pinched between the forming cylinder and the steel ring all the way around the steel ring. The forming cup was placed on top of the base plate of the load cell and firmly seated over the ridge of the base plate. The foot was mechanically lowered into the forming cup with the crosshead speed set at 400 millimeters per minute, crushing the sample while the constant-rate-of-extension tensile testing machine measured the peak load in grams and the energy in gram-mm needed to crush the sample. The average values for peak load and energy for 3 specimens from each sample film-nonwoven laminate material are reported herein.

Trapezoid Trap Tear Strength

The trapezoid trap tearing test measures the tearing strength of fabrics or materials by applying a constantly increasing load in parallel with the length (long dimension) of the test material. This test primarily measures the bonding or interlocking and strength of individual fibers directly in the tensile load. The force required to completely tear the test specimen is measured, with higher numbers indicating a greater resistance to tearing and, therefore, a stronger material.

Six test specimens of 3×6 inches (76×152 mm) were cut from each sample material tested, with three specimens having the longer dimension oriented in the CD and three specimens having the long dimension oriented in the MD. A metal trapezoidal template with parallel sides measuring four inches and one inch, respectively, was placed on each specimen, with the parallel sides aligned with the length of the specimen. An outline of the trapezoid was traced on the specimen with a marking pen. A tear in the specimen was made by marking a ⅝ inch (15.9 mm) long cut extending from the midpoint of the shorter side of the trapezoid inward across the specimen.

The entire width of the specimen along the non-parallel sides was placed within clamps of a constant-rate-of-extension tester, such as a Sintech System 2 Computer Integrated Testing System manufactured by MTS Systems Corporation of Eden Prairie, Minn. The cut in the specimen was centered between the clamps. A continuous load was applied to the specimen, with the crosshead speed set at 12 inches/minute, causing the cut to propagate across the specimen width. The force required to completely tear the specimen was recorded in pounds (force) and converted to grams. Tearing load was calculated as the average of the first and highest peaks recorded, as compared to the average of the lowest and highest peaks, as in ASTM Standard Test D 1117-14. In all other respects, the trapezoid tear test conforms to the specifications of ASTM Standard Test D 1117-14.

Adhesive Bond Area Test/Maximum Spacing Test

The adhesive bond area test measures the portion of a unit area of a surface of the film layer to which a pattern of adhesive areas is applied. The maximum spacing test measures the maximum free path measurement between adhesive areas in the direction of stretching of the film.

Four to six specimens of 5–6 square inches (32–39 square centimeters) were cut from each sample material tested. Each specimen was placed in a small tin and stained with osmium tetroxide ($OsO_4$) vapors by placing the specimen in a glass dessicator having a liquid volume of approximately one gallon ($3.785 \times 10_{-3}$ cubic meters) for a period of 16 hours. The osmium tetroxide was supplied by Ted Pella, Inc. of Redding, Calif. The osmium tetroxide was not dissolved in water.

The stained laminates were peeled open by hand, leaving the stained adhesive on a surface of the film layer of each laminate. The osmium tetroxide de-tackifies and cross-links (strengthens) the adhesive, facilitating delamination of the film and nonwoven layers.

The stained adhesive was imaged in reflected light using a Wild M420 macro instrument available from Leica of Deerfield, Ill., with a FOSTEC fiber optic ringlight. Images were acquired through an Model CCD-72 monochrome camera system available from Dage MTI of Michigan City, Ind., directly into a Princeton Gamma Tech (of Princeton, N.J.) Imagist™ system. The video camera manual controls were used, so that there was no variation in image density due to automatic gain control compensation. The images were thresholded, binarized and analyzed using Princeton Gamma Tech image analysis software. The resulting images were printed out on a Hewlett Packard Paintjet™ printer. The average values for percent bond area and the maximum spacing between adhesive areas in the direction of stretching for Example film-nonwoven laminate materials 1–5 are reported herein.

EXAMPLES

A total of 5 sample adhesively-reinforced film-nonwoven laminates are set forth below. The sample adhesively-reinforced film-nonwoven laminates are designed to illustrate particular embodiments of the present invention and to teach one of ordinary skill in the art the manner of carrying out the present invention.

Example 1

An adhesively-reinforced film-nonwoven laminate according to the present invention was made. The film layer contained, on a total weight percent basis based upon the weight of the film, 50% Dowlex® NG3347A linear low density polyethylene having a melt index of 2.3 (grams per 10 minutes at 190° C.) and a density of 0.917 grams per cubic centimeter (g/cc) and 5% Dow® 640 branch low density polyethylene having a melt index of 2.0 (grams per 10 minutes at 190° C.) and a density of 0.922 g/cc. The blend of polyethylene polymers had a melt index of 1.85 (grams per 10 minutes at 190° C.) and a density of 1.452 g/cc. The Dowlex® and Dow® polymers are available from Dow Chemical U.S.A., of Midland, Mich. The film layer further contained 45% by total weight English China Supercoat™ calcium carbonate ($CaCO_3$) coated with 1% stearic acid, having a 1 micron average particle size and a top cut of 7 microns. The calcium carbonate was obtained from ECCA Calcium Products, Inc. in Sylacauga, Ala., a division of ECC International. The film formulation was blown into a mono-layer film at a melt temperature of 333° F. (168° C.) to produce a film having an initial unstretched gauge of about 1.5 mils (about 54 gsm). The film was heated to a temperature of about 160° F. (71° C.) and the film was stretch-thinned to about 4.0 times its original length to an effective gauge of about 0.46 mil (about 18 gsm) using a machine direction orientation (MDO) unit, Model No. 7200 available from Marshall & Williams of Providence, R.I., operating at a line speed of 500 feet per minute (152 meters per minute). The film was annealed at a temperature of 215° F. (103° C.). The film was breathable as indicated by the WVTR data set forth in Table I below.

The nonwoven layer was an about 0.6 osy ( about 20 gsm) spunbond web formed from extrudable thermoplastic resins of a random copolymer of propylene and ethylene monomers containing about 3.3%, by weight, ethylene monomer and 96.7%, by weight, propylene monomer obtained from Shell Oil Company, having offices in Houston, Tex., under the product designation 6D43. The spunbond filaments were essentially continuous in nature and had an average fiber size of 2.2 dpf. The spunbond web was thermally pre-bonded using a pattern of discrete bond points and had a percent bond area of about 15% per unit area of the web.

The film and nonwoven layers were laminated together using a butene copolymer of atactic polypropylene adhesive available from Rexene Corp. of Dallas, Tex., under the product designation Rextac RT2730. The adhesive was applied to the film layer in the form of randomly dispersed meltblown adhesive fibers, using conventional meltblown apparatus essentially as described in U.S. Pat. No. 4,720,252, the disclosure of which is incorporated herein by reference. The adhesive was heated to about 350° F. (177° C.) and applied to the film at an air temperature of about 430° F. (221° C.), an air pressure of about 20 psig (1.41 kilograms per square centimeter), a forming height of about 3.0 inches (76.2 mm) and a line speed of about 300 feet per minute (91 meters per minute). The adhesive-bearing film layer and nonwoven layer were bonded together by passing through a nip formed by counter-rotating smooth rolls. The distance between the point of adhesive application to the film layer and the bonding nip wherein the adhesive-bearing film layer and the nonwoven layer were joined was about 13 inches (33.0 cm). The adhesive add-on amount was about 1.5 gsm and the maximum spacing of the adhesive areas in the direction of stretching of the film layer was about 0.5 inch (12.7 mm). The average percent bond area was about 18 percent. The resultant film-nonwoven laminate had a basis weight of 1.22 osy ( about 40.8 gsm).

Example 2

An adhesively-reinforced film-nonwoven laminate according to the present invention was made. The film layer contained, on a total weight percent basis based upon the weight of the film, 45% Dowlex® NG3347A linear low density polyethylene and 55% by total weight English China Supercoat™ calcium carbonate ($CaCO_3$), both as described in detail in Example 1 above. The film formulation was cast into a mono-layer film at a melt temperature of 360° F. (182° C.) to produce a film having an initial unstretched gauge of about 1.5 mils (about 54 gsm). The film was heated to a temperature of about 160° F. (71° C.) and the film was stretch-thinned to about 4.7 times its original length to an effective gauge of about 0.46 mil (about 18 gsm) using an MDO unit as described in Example 1 above operating at a line speed of 500 feet per minute (152 meters per minute). The film was annealed at a temperature of 200° F. (93° C.). The film was breathable as indicated by the WVTR data set forth in Table I below.

The nonwoven layer was the same as described in Example 1 above.

The film and nonwoven layers were laminated together using a pigmented block-copolymer pressure sensitive adhesive available from National Starch and Chemical Corp., having offices in Bridgewater, N.J., under the product designation Dispomelt® NS34-5610. The adhesive was applied to the film layer by first printing the adhesive in a cloud pattern as shown in FIG. 4 hereof to a suitable release paper and then transferring the adhesive to the film layer surface, using a conventional screen printing and transfer process. The adhesive was applied to the release paper at a line speed of about 25–50 feet per minute (7.6–15.2 meters per minute) and the adhesive was transferred to the film layer at a line speed of 300 feet per minute (91 meters per minute). The adhesive-bearing film layer and nonwoven layer were bonded together by passing through a nip formed by counter-rotating smooth rolls. The adhesive add-on amount was about 9.0 gsm and the maximum spacing of the adhesive areas in the direction of stretching of the film layer was about 1.0 inch (25.4 mm). The average percent bond area was about 12 percent. The resultant film-nonwoven laminate had a basis weight of about 47.0 gsm.

Example 3

An adhesively-reinforced film-nonwoven laminate according to the present invention was made. The film layer and nonwoven layer both were the same as described in Example 2 above.

The film and nonwoven layers were laminated together using the same adhesive as described above in Example 2. The adhesive was applied to the film layer by first printing the adhesive in a ribbed pattern as shown in FIG. 3 hereof to a suitable release paper and then transferring the adhesive to the film layer surface, as described above in Example 2. The adhesive was applied to the release paper at a line speed of about 25–50 feet per minute (7.6–15.2 meters per minute) and the adhesive was transferred to the film layer at a line speed of 300 feet per minute (91 meters per minute). The adhesive-bearing film layer and nonwoven layer were bonded together by passing through a nip formed by counter-rotating smooth rolls. The adhesive add-on amount was about 17.0 gsm and the maximum spacing of the adhesive areas in the direction of stretching of the film layer was about 0.25 inch (6.35 mm). The average percent bond area was about 22 percent. The resultant filmnonwoven laminate had a basis weight of about 56.3 gsm.

Example 4

An adhesively-reinforced film-nonwoven laminate according to the present invention was made. The film layer was the same as described above in Example 2. The nonwoven layer was an about 0.5 osy (about 17 gsm) spunbond web formed from extrudable thermoplastic polypropylene fibers obtained from Exxon Corp., having offices in Houston, Tex., under the product designation 3445. The spunbond filaments were essentially continuous in nature and had an average fiber size of 2.2 dpf. The spunbond web was thermally pre-bonded using a pattern of discrete bond points and had a percent bond area of about 15% per unit area of the web.

The film and nonwoven layers were laminated together using an 18% vinyl acetate copolymer of an ethylene-vinyl acetate adhesive available from E. I. DuPont de Nemours of Wilmington, Del., under the product designation Elvax 410. This adhesive was screen printed directly onto the film layer in the ribbed pattern shown in FIG. 3 hereof. The adhesive was applied to the film layer at a line speed of about 25–50 feet per minute (7.6–15.2 meters per minute). The adhesive-bearing film layer and nonwoven layer were bonded together by passing through a nip formed by counter-rotating smooth rolls. The distance between the point of adhesive application to the film layer and the bonding nip wherein the adhesive-bearing film layer and the nonwoven layer were joined was about 23 inches (58.4 cm). The adhesive add-on amount was about 1.0 to 2.0 gsm and the maximum spacing of the adhesive areas in the direction of stretching of the film layer was about 0.25 inch (6.35 mm). The average percent bond area was about 22 percent. The resultant film-nonwoven laminate had a basis weight of about 37.3 gsm.

Example 5

An adhesively-reinforced film-nonwoven laminate according to the present invention was made. The film and nonwoven layers and the adhesive used were the same as described above in Example 2, except the adhesive was non-pigmented.

The adhesive was applied to the film layer using a Control Coat™ spray adhesive pattern applicator available from Nordson Corp., having offices in Norcross, Ga., under the product designation Metered Control Coat™ Applicator. The adhesive was heated to about 350° F. (177° C.) and applied to the film at an air temperature of about 380° F. (193° C. an air pressure of about 80 psig (5.63 kg/cm$^2$), a forming height of about 1.0 inch (25.4 mm) and a line speed of about 400 feet per minute (120 meters per minute). The adhesive-film layer and nonwoven layer were bonded together by passing through a nip by counter-rotating smooth rolls. The distance between the point of adhesive on to the film layer and the bonding nip wherein the adhesive-bearing film layer nonwoven layer were joined was about 23 inches (58.4 cm). The adhesive add-on was about 2.0 gsm and the maximum spacing of the adhesive areas in the of stretching of the film layer was about 0.1 inch (2.54 mm). The average percent a was about 15 percent. The resultant film-nonwoven laminate had a basis weight 42.4 gsm.

TABLE I

| EXAMPLE | MD TENSILE STRENGTH (grams) | MD PERCENT ELONGATION AT BREAK (%) | CD TENSILE STRENGTH (grams) | CD PERCENT ELONGATION AT BREAK (%) | WVTR (g/m$^2$/24 hours) | HYDRO HEAD (cm) |
|---|---|---|---|---|---|---|
| 1 | 8260 | 75 | 4120 | 75 | 890 | 170 |
| 2 | 8928 | 58 | 3371 | 84 | 3563 | 140 |
| 3 | 9836 | 75 | 4101 | 93 | 2892 | 159 |
| 4 | 8118 | 47 | 4603 | 43 |  | 180 |
| 5 | 10893 | 83 | 3873 | 82 | 3876 | 177 |

TABLE II

| EXAMPLE | PEEL STRENGTH (grams) | CUP CRUSH ENERGY (grams/mm) | CUP CRUSH LOAD (grams) | MD TRAP TEAR STRENGTH (grams) | CD TRAP TEAR STRENGTH (grams) |
|---|---|---|---|---|---|
| 1 | 560 | 1649 | 84 | 3677 | 1662 |
| 2 | 1328 | 987 | 57 | 2815 | 1440 |
| 3 | NA* | 1255 | 66 | 3985 | 1580 |
| 4 | 130 | 1117 | 58 | 2137 | 995 |
| 5 | 254 | 1465 | 74 | 3285 | 1768 |

*NA indicates film and nonwoven layers that could not be manually separated.

For comparison purposes, and more specifically, to isolate the impact of adhesive-reinforcement on the strength and durability of the film layer incorporated into the film-nonwoven laminate of the present invention, the following data was gathered for the film layers described in Examples 1–5 herein, as well as for the film layer of a film-nonwoven laminate from a commercially available absorbent article.

COMPARATIVE EXAMPLES

Comparative Example 1

This film layer was the same as described in Example 1, with no adhesive areas applied.

Comparative Example 2

This film layer was the same as described in Example 1, with the same adhesive type and pattern applied as described in Example 1.

Comparative Example 3

This film layer was the same as described in Example 2, with no adhesive areas applied.

Comparative Example 4

This film layer was the same as described in Example 2, with the same adhesive type and pattern applied as described in Example 2.

Comparative Example 5

This film layer was the same as described in Example 3, with the same adhesive type and pattern applied as described in Example 3.

Comparative Example 6

This film layer was the same as described in Example 5, with the same adhesive type and pattern as described in Example 5.

Comparative Example 7

This non-breathable film layer was obtained from the film-nonwoven laminate outer cover of a disposable diaper sold commercially by Kimberly-Clark Corporation, the assignee of the present invention, under the product designation Huggies® Ultratrim diapers. No adhesive was applied to this film layer. The film layer had an effective gauge of about 0.41 mil.

applied demonstrates the reinforcement function of the adhesive areas.

Finally, the data for Comparative Example 7 establish that the adhesively-reinforced film layers that are incorporated into the film-nonwoven laminate of this invention are at least comparable in strength and toughness to commercially available film layers.

It is contemplated that the adhesively-reinforced film-nonwoven laminate constructed in accordance with the present invention will be tailored and adjusted by those of ordinary skill in the art to accommodate various levels of performance demand imparted during actual use. Accordingly, while this invention has been described by reference to certain specific embodiments and examples, it will be understood that this invention is capable of further modifications. This application is, therefore, intended to cover any variations, uses or adaptations of the invention following the general principles thereof, and including such departures from the present disclosure as come within known or customary practice in the art to which this invention pertains and fall within the limits of the appended claims.

What is claimed is:

1. An adhesively-reinforced film-nonwoven laminate comprising:

a first fibrous nonwoven layer having a surface;

a film layer having a first surface;

said film layer being oriented in a direction of stretching and having an effective gauge of 0.6 mil or less;

said film layer being formed from a blend including, on a total weight percent basis based upon the total weight of the film layer, from about 30 percent to about 70 percent of a first polyolefin polymer, from about 70 percent to about 30 percent of a filler, and from about 0 to about 20 percent of a second polyolefin polymer;

said film layer having a water vapor transmission rate of at least about 300 grams per square meter per 24 hours;

a pattern of adhesive areas applied to said first surface of said film layer;

said pattern of adhesive areas having an add-on amount of from about 0.1 to about 20 grams per square meter, a percent bond area of from about 5 percent to about 50 percent per unit area of said surface of said film layer,

TABLE III

| COMP. EXAMPLE | MD TENSILE STRENGTH (grams) | MD PERCENT ELONGATION AT BREAK (%) | CD TENSILE STRENGTH (grams) | CD PERCENT ELONGATION AT BREAK (%) | WVTR (G/M²/24 hours) |
|---|---|---|---|---|---|
| 1 | 4850 | 150 | 830 | 500 | 1240 |
| 2 | 6300 | 162 | 870 | 550 | |
| 3 | 8444 | 135 | 698 | 265 | 3800 |
| 4 | 6212 | 101 | 525 | 323 | 3471 |
| 5 | 6800 | 114 | 669 | 427 | 3827 |
| 6 | 5448 | 96 | 585 | 517 | 3631 |
| 7 | 2500 | 180 | 840 | 450 | 70 |

The data for Comparative Examples 1–6 clearly illustrate the impact application of adhesive areas as described herein has on the strength and toughness or durability of the film layers alone. Particularly in the cross machine direction, the direction in which uniaxially, machine direction oriented films typically do not have good toughness or durability, the increase in percent elongation at break values as between the virgin films and those same films to which adhesive areas are and a maximum spacing between adhesive areas in a direction generally parallel to said direction of stretching of about 1.0 inch or less;

said surface of said fibrous nonwoven layer being adhered to said first surface of said film layer by said pattern of adhesive areas applied to said first surface of said film layer to form a laminate.

2. The adhesively-reinforced film-nonwoven laminate of claim 1 wherein said laminate has a cross machine direction tensile strength of at least 3000 grams.

3. The adhesively-reinforced film-nonwoven laminate of claim 1 wherein said laminate has a cross machine elongation at break of at least 35%.

4. The adhesively-reinforced film-nonwoven laminate of claim 1 wherein said laminate has a water vapor transmission rate of at least about 1000 grams per square meter per 24 hours.

5. The adhesively-reinforced film-nonwoven laminate of claim 1 wherein said laminate has a peel strength of at least 100 grams.

6. The adhesively-reinforced film-nonwoven laminate of claim 1 wherein said laminate has a cup crush load of less than 100 grams.

7. The adhesively-reinforced film-nonwoven laminate of claim 1 wherein said laminate has a cross machine direction tear strength of at least 950 grams.

8. The adhesively-reinforced film-nonwoven laminate of claim 1 wherein said maximum spacing between said adhesive areas in a direction generally parallel to said direction of stretching is about 0.25 inch or less.

9. The adhesively-reinforced film-nonwoven laminate of claim 1 wherein said maximum spacing between said adhesive areas in a direction generally parallel to said direction of stretching is about 0.125 inch or less.

10. The adhesively-reinforced film-nonwoven laminate of claim 1 wherein said adhesive add-on amount is from about 0.25 to about 5.0 grams per square meter.

11. The adhesively-reinforced film-nonwoven laminate of claim 1 wherein said adhesive add-on amount is from about 0.5 to about 1.5 grams per square meter.

12. The adhesively-reinforced film-nonwoven laminate of claim 1 wherein said percent bond area is from about 5 percent to about 35 percent.

13. The adhesively-reinforced film-nonwoven laminate of claim 1 wherein said first fibrous nonwoven layer comprises a laminate.

14. The adhesively-reinforced film-nonwoven laminate of claim 13 wherein said first nonwoven layer comprises a spunbond-meltblown-spunbond laminate.

15. The adhesively-reinforced film-nonwoven laminate of claim 13 wherein said first nonwoven layer comprises a spunbond-meltblown laminate.

16. The adhesively-reinforced film-nonwoven laminate of claim 1 further comprising a second fibrous nonwoven layer having a surface wherein said second fibrous nonwoven layer is bonded to a second surface of said film layer opposite said first fibrous nonwoven layer.

17. The adhesively-reinforced film-nonwoven laminate of claim 1 wherein said first polyolefin polymer comprises a predominately linear polyolefin polymer.

18. The adhesively-reinforced film-nonwoven laminate of claim 17 wherein said predominately linear polyolefin polymer comprises linear low density polyethylene.

19. An absorbent article comprising:

a liner;

a backsheet;

an absorbent core disposed between said liner and said backsheet;

said backsheet comprising the adhesively-reinforced film-nonwoven laminate of claim 1.

20. An article of clothing comprising the adhesively-reinforced film-nonwoven laminate of claim 1.

21. A surgical drape comprising the adhesively-reinforced film-nonwoven laminate of claim 1.

22. A sterilization wrapper comprising the adhesively-reinforced film-nonwoven laminate of claim 1.

* * * * *